United States Patent [19]
Strähle

[11] Patent Number: 5,891,015
[45] Date of Patent: Apr. 6, 1999

[54] ENDOSCOPE INCLUDING A FRONT LENS GROUP AND AN INNER LENS GROUP FORMING A TELESYSTEM

[75] Inventor: Fritz Strähle, Heubach-Lautern, Germany

[73] Assignee: Carl-Zeiss-Stiftung, Heidenheim, Germany

[21] Appl. No.: 788,994

[22] Filed: Jan. 27, 1997

Related U.S. Application Data

[63] Continuation of Ser. No. 421,851, Apr. 14, 1995, abandoned.

[30] Foreign Application Priority Data

Apr. 14, 1994 [DE] Germany .......................... 44 12 861.4

[51] Int. Cl.$^6$ ..................................... A61B 1/002
[52] U.S. Cl. ......................... 600/160; 600/138; 600/167; 359/434
[58] Field of Search .................................... 600/136, 138, 600/160, 167, 168, 171, 172, 176; 359/434, 435

[56] References Cited

U.S. PATENT DOCUMENTS

| | | |
|---|---|---|
| 1,706,930 | 3/1929 | Loeck . |
| 3,005,452 | 10/1961 | Pitman . |
| 4,036,218 | 7/1977 | Yamashita et al. . |
| 4,643,541 | 2/1987 | Matsubara . |
| 4,757,805 | 7/1988 | Yabe . |
| 4,916,534 | 4/1990 | Takahashi et al. . |
| 4,964,710 | 10/1990 | Leiner . |
| 5,188,092 | 2/1993 | White . |
| 5,263,110 | 11/1993 | Anderson ................................. 385/117 |
| 5,396,366 | 3/1995 | Brown et al. ........................... 359/117 |
| 5,457,576 | 10/1995 | Atkinson et al. ....................... 359/654 |
| 5,632,718 | 5/1997 | Igarashi et al. ......................... 600/160 |

FOREIGN PATENT DOCUMENTS

| | | |
|---|---|---|
| 238723 | 9/1986 | Germany . |
| 4207092 | 9/1993 | Germany . |
| 0520974 | 7/1976 | U.S.S.R. . |
| WO 93/15647 | 8/1993 | WIPO . |
| WO 94/14367 | 7/1994 | WIPO . |

*Primary Examiner*—John P. Leubecker
*Attorney, Agent, or Firm*—Walter Ottesen

[57] ABSTRACT

The invention is directed to an endoscope having an especially simple optical system within an endoscope tube 22. The imaging system of the endoscope tube includes a front group 25 having a negative refractive power and an inner group 28 having a positive refractive power. The front group 25 and the inner group 28 conjointly define a telescope system which permits the object plane 24 to be imaged in the intermediate image plane 32 without intermediate imaging at a distance of 200 mm to 600 mm from the distal end of the endoscope tube 22. Otherwise, only glass rods having planar-parallel end faces are mounted within the endoscope tube. A field optic is preferably a part of the viewing component. An adequate transmission and correction with respect to chromatic and monochromatic imaging errors is possible notwithstanding the simple optical configuration. The front group and inner group can also be configured as aspherical individual lenses. The endoscope is especially useable as a disposable endoscope because of the simple configuration of the optic.

23 Claims, 7 Drawing Sheets

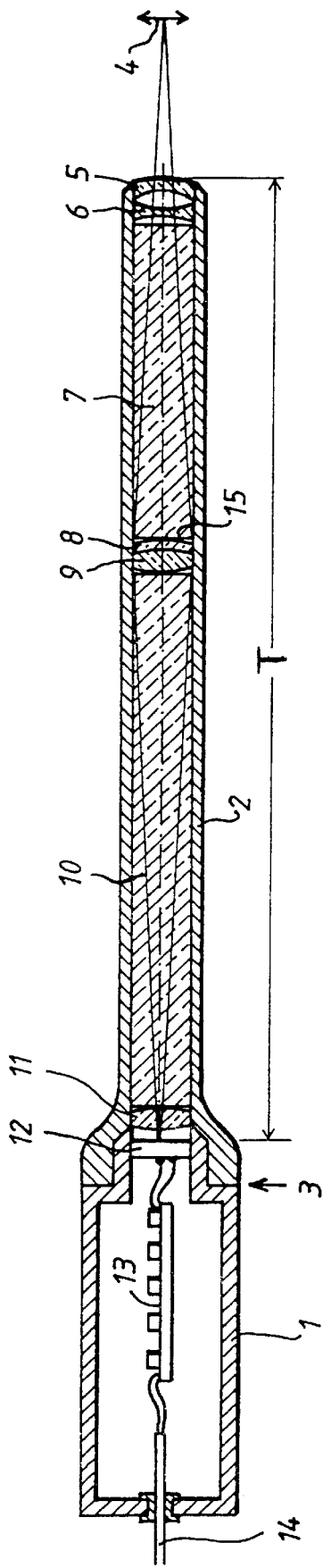
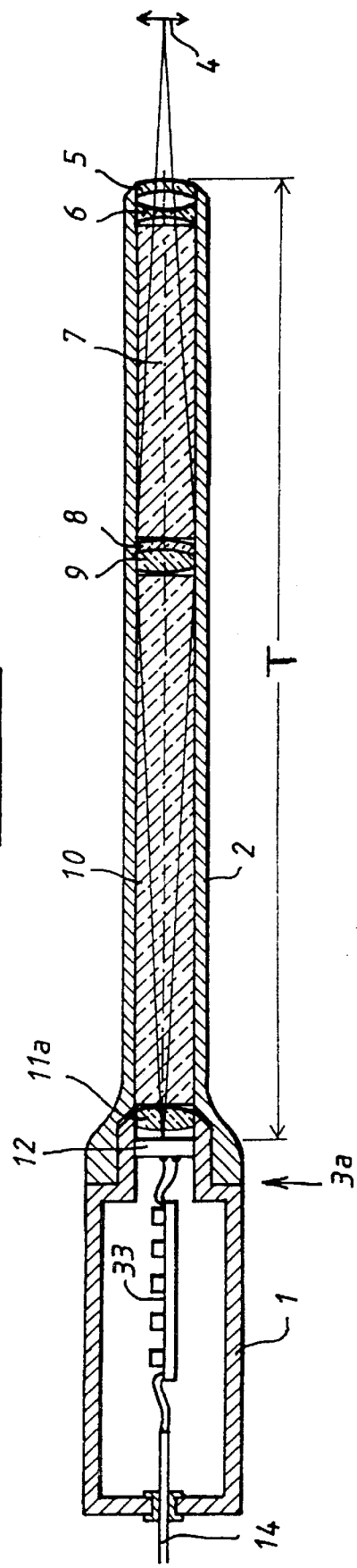

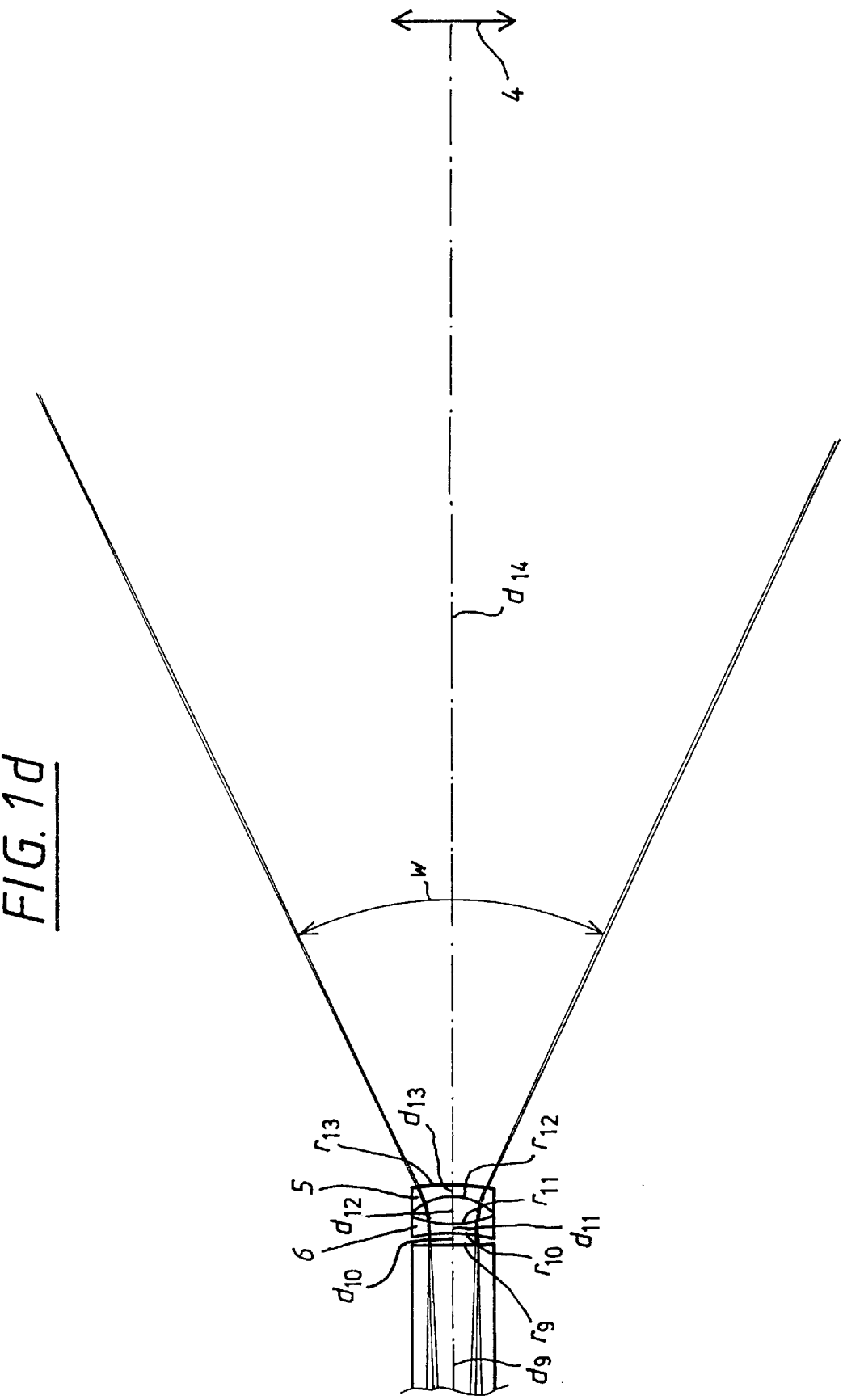

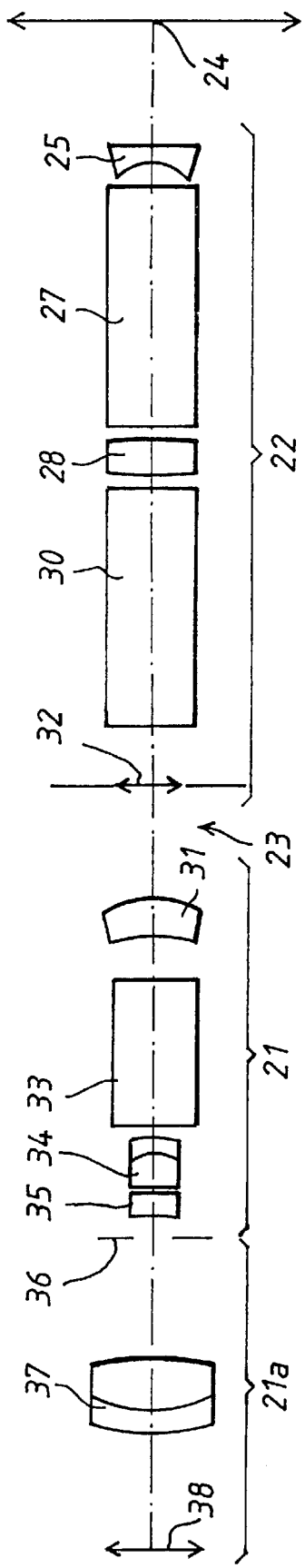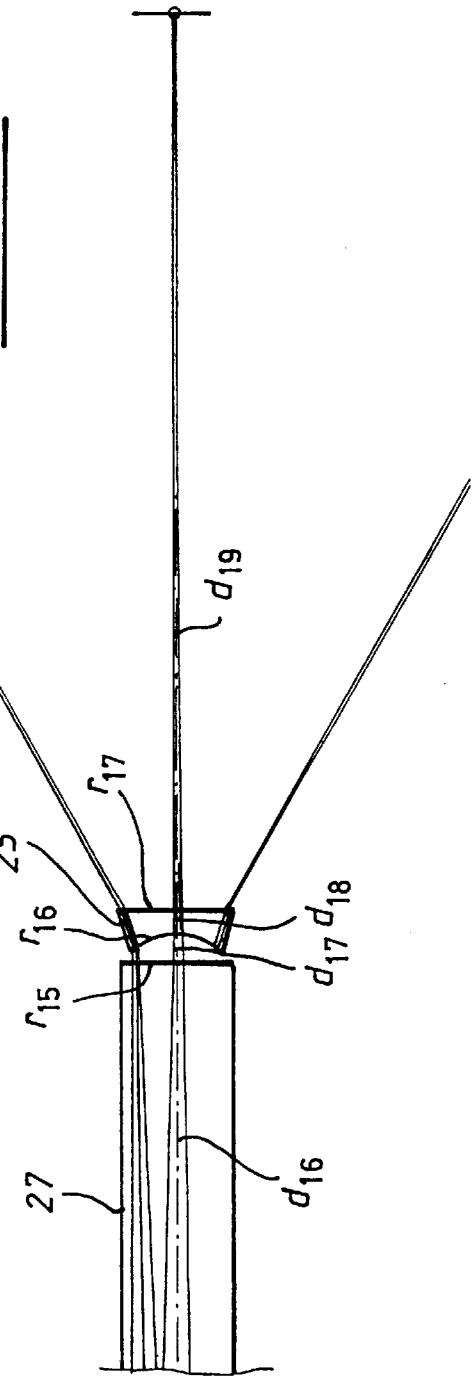
FIG.2a
FIG.2d

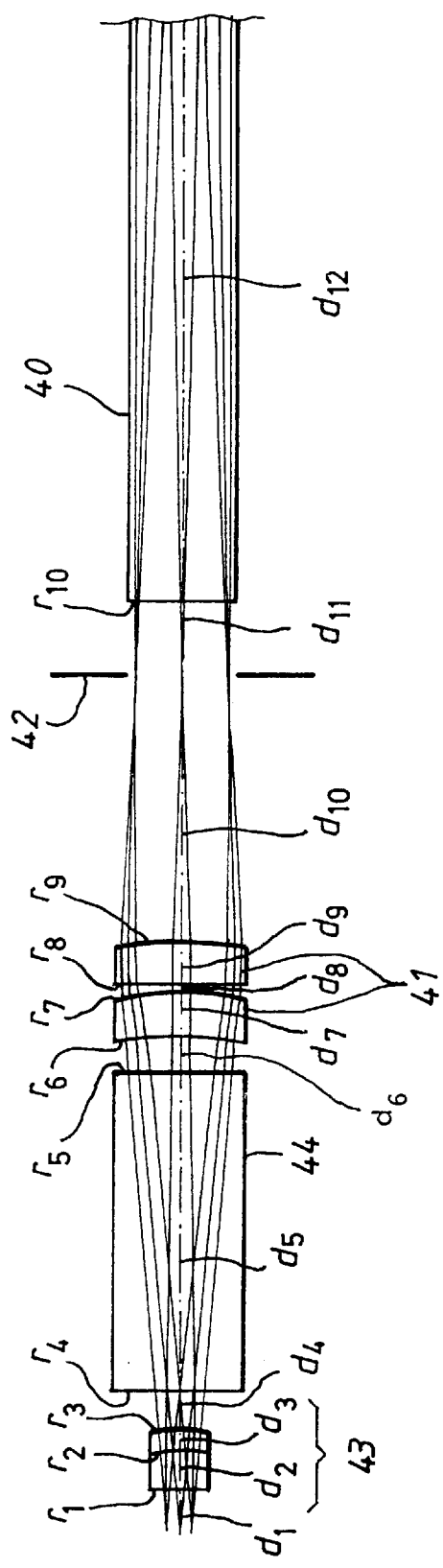
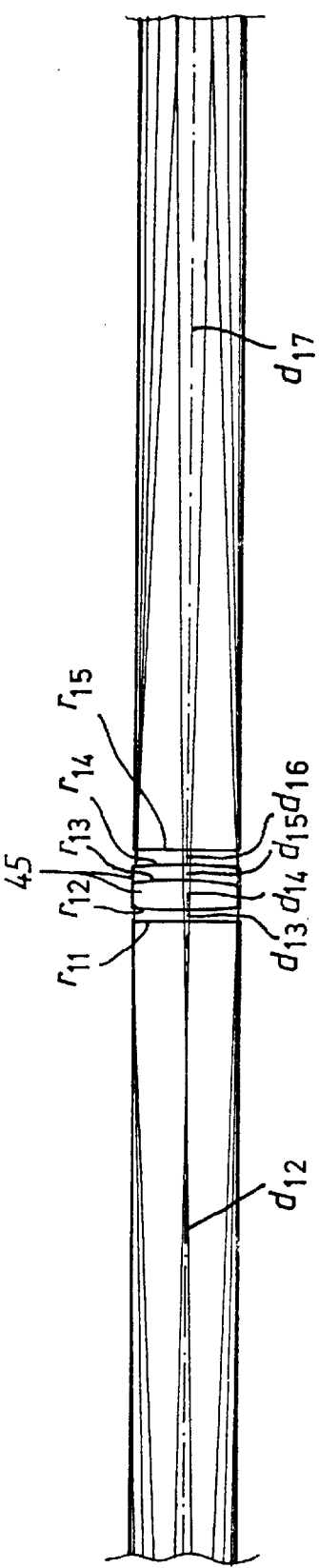

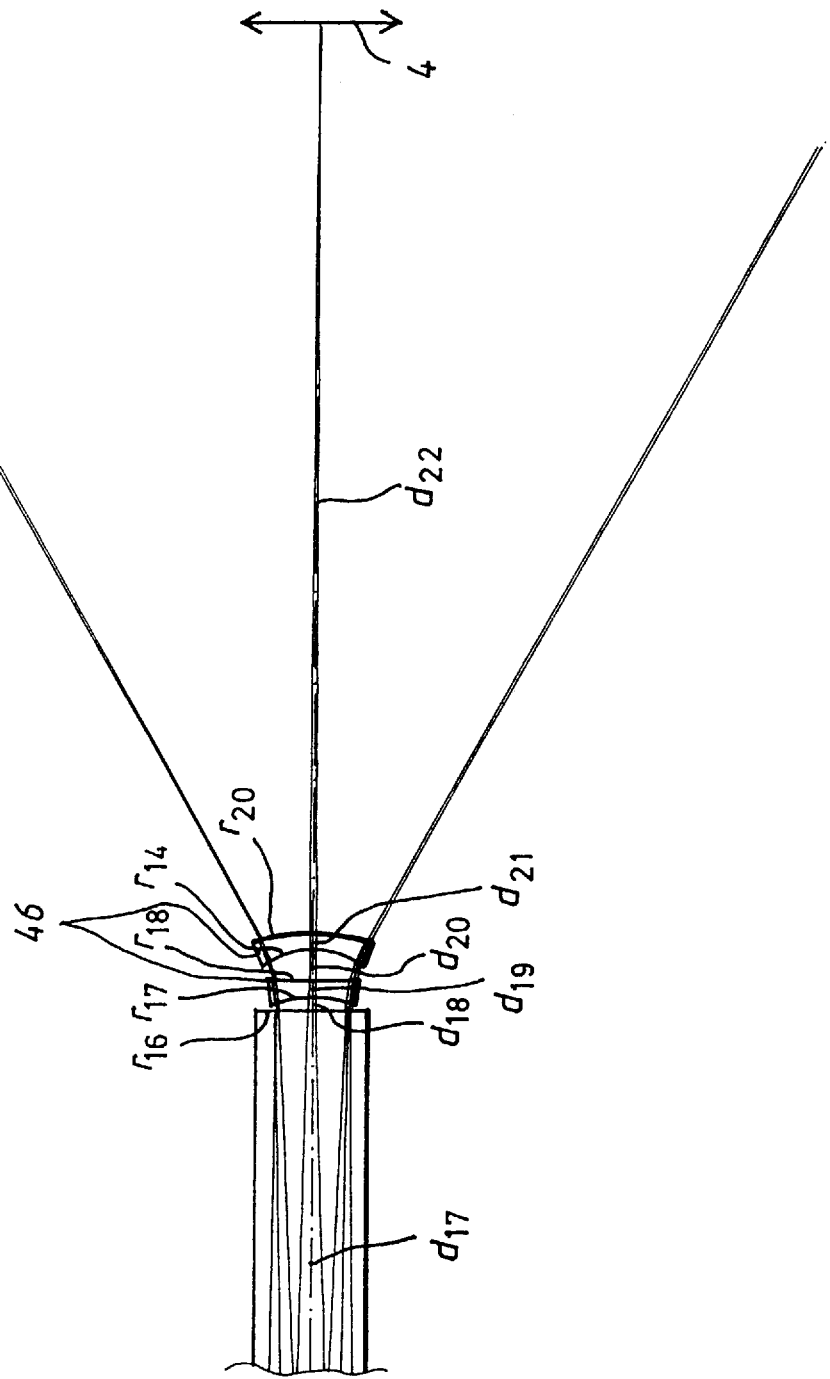

ENDOSCOPE INCLUDING A FRONT LENS GROUP AND AN INNER LENS GROUP FORMING A TELESYSTEM

This is a continuation of application Ser. No. 08/421,851, filed on Apr. 14, 1995 now abandoned.

FIELD OF THE INVENTION

The invention relates to an endoscope having a viewing component and an endoscope tube component containing an imaging optic of simple configuration. The invention relates especially to a so-called disposable endoscope wherein the endoscope tube component can be separated from the viewing component for the one-time use of the tube component.

BACKGROUND OF THE INVENTION

Disposable endoscopes are used once and then discarded. Disposable endoscopes are becoming increasingly significant for medical applications because the repeated sterilization of the critical components, which come into direct contact with the patient, is eliminated. An important criterion for disposable endoscopes is that a simple and low-cost optic be provided in the endoscope tube. At the same time, however, a high imaging performance of the endoscope system is required. Above all, this is characterized by the transmission or brightness and an optimal correction of aberrations. At the same time, and depending upon the area of application, tube lengths of between 200 and 600 mm with a tube diameter of less than 10 mm are desirable.

Disposable endoscopes are described, for example, in U.S. Pat. Nos. 5,188,092 and 4,964,710 as well as in PCT publication WO 93/15647. For low-cost optics, plastic lenses are used exclusively in the endoscope tube as described in PCT publication WO 93/15647. Very considerable limitations occur with respect to the correction of imaging errors in this context because the selection of available materials is minimal at the present time. Furthermore, plastic lenses do not yet satisfy the requirements with respect to the quality of the refracting surfaces and the homogeneity of the medium. In the endoscope disclosed in U.S. Pat. No. 5,188,092, these present-day problems are avoided by utilizing pressure molded glass lenses. Furthermore, a simplified assembly technique is suggested.

These known optical systems are, however, very complex. Several multi-lens intermediate imaging systems are always required in order to achieve the tube length desired for medical applications. In one embodiment of the endoscope disclosed in PCT publication WO 93/15647, a double-lens objective is, for example, provided at the distal end of the endoscope tube and three intermediate imaging systems are arranged within the endoscope tube. Each of the intermediate imaging systems includes six lenses. Even when each individual lens itself is relatively inexpensive in comparison to the glass lenses classically produced by grinding and polishing, the total number of the lenses mounted in the endoscope tube lead, however, to a considerable cost of the exchangeable component.

Endoscopes have already been proposed wherein a CCD-camera chip is mounted at the distal region of the endoscope tube directly behind the endoscope objective. The viewing field is then imaged on the CCD-camera chip without previous intermediate imaging. In this way, a significantly simpler optical configuration is achieved because the optical image does not have to be guided over a longer path. Such an endoscope is, for example, disclosed in U.S. Pat. No. 4,757,805. This apparatus concept is, however, unsuitable for a disposable endoscope because the rather expensive CCD chip is included in the disposable parts.

Published German patent application 4,207,092 discloses an endoscope containing the following in the endoscope tube: a double-lens objective, two intermediate imaging systems each of which is configured as a rod lens and an image collimating lens. This published patent application, however, provides no optical data whatsoever or information as to the length of the endoscope tube.

U.S. patent application Ser. No. 08/100,276, filed Jul. 28, 1993, discloses a stereoendoscope including a distal front group having a negative diffractive power. The stereoendoscope, together with an intermediate group having a positive diffractive power, generates a real image of the object. However, here too the first real intermediate image of the object lies already at a distance of approximately 150 mm behind the front group. In order to achieve a tube length desired for endoscopy, it is here therefore also necessary to still provide at least a second intermediate image within the endoscope tube.

SUMMARY OF THE INVENTION

It is an object of the invention to provide an endoscope wherein the optic mounted in the endoscope tube is simple and has a cost-effective configuration and therefore is suitable for a disposable endoscope.

The endoscope of the invention is for viewing an object and includes: a viewing component and an endoscope tube component; the components conjointly defining an optical axis; the endoscope component including a tube and an imaging optic arrangement mounted in the tube; the imaging optic arrangement including a distal front lens group and an inner lens group; the front lens group and the inner lens group conjointly defining an optical system for forming an image of the object in a real image plane or an intermediate image plane located a distance (T) from the front lens group; and, the distance (T) being in the range of 200 to 600 mm.

In the endoscope according to the invention, the imaging optic includes a distal front group and an inner group. The materials and surface-curvature radii of the lenses are so selected in these groups that the first real image plane or intermediate image plane of the object is at a distance of between 200 and 600 mm from the distal front group.

In many endoscopes, conventional optics have been retained which are complex because of the number of lenses and the complexity is reduced only by utilizing cheaper components. In contrast to this development of recent times, it has been recognized in accordance with the invention that an image transmission over the desired distance is possible with very few optical elements and with high optical quality and adequate brightness even when intermediate images within the endoscope tube are omitted.

The front group preferably has a negative diffraction power and the inner group a positive diffraction power so that both groups conjointly define a so-called telesystem wherein the intercept distance is less than the focal length of the system.

In this telesystem, the distance of the inner group from the distal front group is less than the distance of the inner group from the real image plane or intermediate image plane. Notwithstanding the simple configuration of the imaging optic, an adequately large aperture, and therefore a high brightness, are achieved. Furthermore, vignetting is avoided by optimal pupil imaging.

For simple and cost-effective endoscopes, the imaging optic in the endoscope tube includes less than seven lenses and, in especially simple configurations, five or even only two lenses are provided. The inner group then comprises only a single composite lens or an aspherical biconvex or planar-convex single lens. The relevant monochromatic imaging errors such as spherical aberration, coma and axial chromatic aberration are corrected by this inner group. Most of all, the imaging errors in the field, such as image-field convexity, astigmatism and chromatic magnification error are compensated by the front group coacting with a field optic. Overall, an optimally corrected image then results.

The use of an imaging optic having fewer than five elements is especially then possible when the proximal field optic is mounted in the vicinity of the generated image or intermediate image within the viewing component and therefore does not belong to the exchangeable parts.

Glass rods having planar end faces are mounted between the lenses to lengthen the endoscope tube. The additional complexity associated with such glass rods is very minimal in comparison to utilizing rod lenses because glass rods having planar end faces can be manufactured easily and cost-effectively.

According to another feature of the invention, the imaging optic arrangement can include a field lens mounted in the tube of the endoscope tube component. The field lens is then mounted adjacent the inner lens group. A first glass rod is then mounted in the tube between the distal front lens and the inner lens group and a second glass rod is mounted in the tube between the inner lens group and the field lens.

The distal element of the front member preferably comprises an acid-resistant glass. For this purpose, the dense barium crown glasses SK2 and SK5 manufactured by Schott Glaswerke of Mainz, Germany have been shown to be very effective.

In an especially simple embodiment, the distal front group comprises a planar-concave aspherical lens with the planar face thereof being distally arranged. The planar face simultaneously acts as a distal end window of the endoscope tube. In this way, the endoscope can also be dipped into body fluids without the imaging power being affected. However, comparable imaging powers can be also achieved by replacing the aspherical lens with two spherical individual lenses having a negative refractive power.

According to another embodiment of the invention, the viewing component and endoscope tube component conjointly define an interface transverse to the axis whereat the components are mutually connected and disconnected.

The optical manufacturing data such as radius of curvature $r_i$, thickness or distance $d_i$ and the glasses used are listed in Tables I, II and III. The thicknesses and distances $d_i$ are measured on the optical axis. The glasses used are identified by the commercial designations of Schott Glaswerke of Mainz, Germany.

BRIEF DESCRIPTION OF THE DRAWINGS

The invention will now be described with reference to the drawings wherein:

FIG. 1a shows a first embodiment of the endoscope according to the invention wherein the imaging optic includes five elements within the endoscope tube;

FIGS. 1b to 1d are a set of schematics of lens sections showing details of the endoscope of FIG. 1a;

FIG. 1e is a schematic of an alternate configuration of the embodiment of FIGS. 1a to 1d wherein the field optic is a component of the viewing system;

FIG. 2a is a schematic showing a second embodiment of the endoscope of the invention wherein the imaging optic includes two elements within the endoscope tube;

FIGS. 2b to 2d are a set of lens section schematics showing details of the embodiment of the endoscope of FIG. 2a; and, FIGS. 3a to 3c show lens sections of a further embodiment having an imaging optic including four elements mounted in the endoscope tube.

Figure 1B:
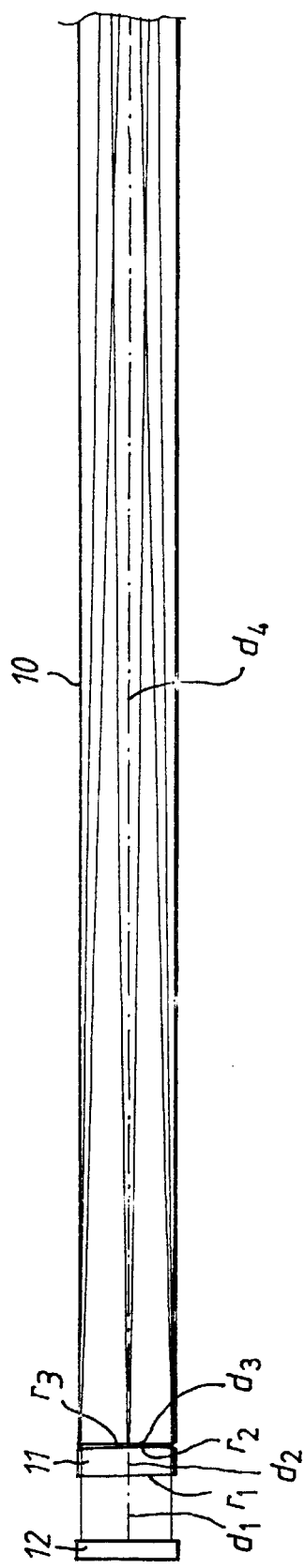

DESCRIPTION OF THE PREFERRED
EMBODIMENTS OF THE INVENTION

The endoscope of FIG. 1a includes a viewing component 1 and an endoscope tube 2. The viewing component 1 and the endoscope tube 2 can be separated from each other at the interface 3. The endoscope tube 2 is configured as a disposable component which is used only once and is then discarded; whereas, the viewing component 1 is provided to be used many times. For this purpose, the endoscope tube 2 is exchanged for another endoscope tube 2 which can have completely different optical performance data.

A five-element imaging optic is mounted in the endoscope tube 2. This imaging optic comprises a two-element front group (5, 6) having a negative refractive power, an inner two-element composite lens (8, 9) having positive refractive power and a field lens configured as a single lens 11. Both elements of the front group (5, 6) each have a negative refractive power. A first glass rod 7 is provided between the front group (5, 6) and the inner composite lens (8, 9) and a second glass rod 10 is provided between the inner composite lens (8, 9) and the field lens 11. The glass rods (7, 10) have plane-parallel end faces and are provided for extending the length of the tube. All essential distances within the endoscope tube are filled with glass by utilizing these glass rods (7, 10).

The front group (5, 6) and the inner composite lens (8, 9) conjointly define a telesystem which images the object 4 directly onto the CCD-camera chip mounted in the image plane 12 without intermediate imaging. The structural length of the endoscope tube 2 is the distance T between the distal front face of the front group 5 and the image plane 12. In this embodiment, the distance T is 479 mm. In this way, the endoscope can be used during surgery deep in the interior of the body. The distance between the inner composite lens (8, 9) and the front group (5, 6) is here less than the distance between the inner composite lens (8, 9) and the image plane which is coincident with the camera sensor. In this way, a relatively large aperture is achieved notwithstanding the simple configuration of the imaging optic within the endoscope tube 2.

The camera sensor is already a part of the viewing component and therefore can be used many times. A circuit board 13 is mounted within the viewing component and includes the read-out electronics for the camera sensor and a first signal amplifier. The preamplified video signals are then conducted out of the viewing component via electrical leads 14 and displayed on a monitor in a conventional manner.

Figure 1C:
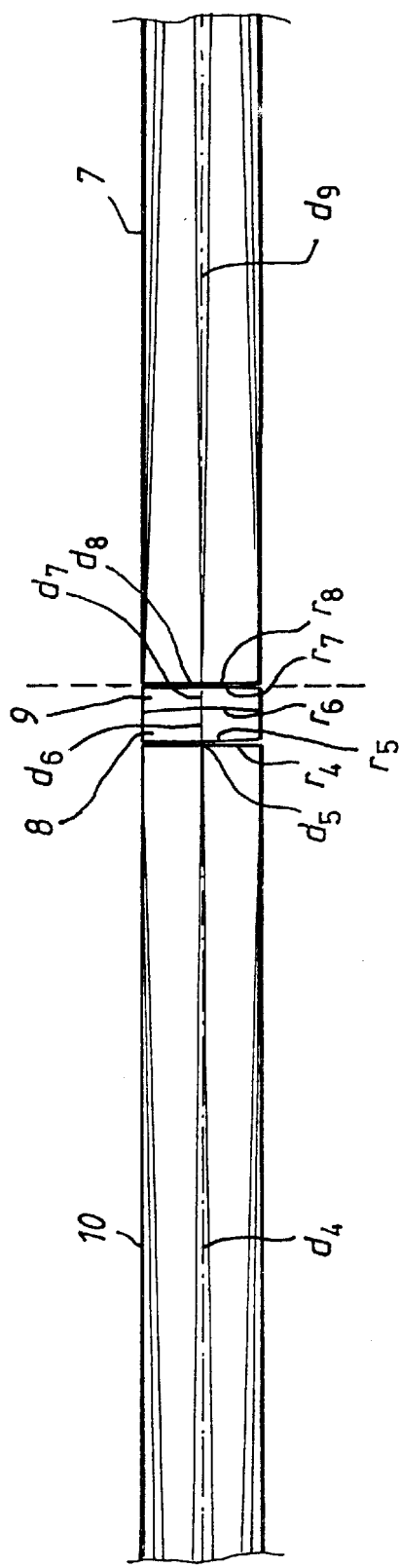

The detailed assembly of the imaging optic within the endoscope tube 2 is shown in the lens section schematics of FIGS. 1b to 1d. FIG. 1b shows the region of the field lens 11 and FIG. 1c shows the region of the inner composite lens (8, 9) and FIG. 1d shows the region of the front group (5, 6). The distances $d_4$ and $d_9$ of the respective intermediate-lying glass rods (7, 10) as well as the distance $d_{14}$ between the distal element 5 and the object plane 4 are shortened to provide an overview. The corresponding optical manufacturing data are shown in Table I. Here, reference character $r_i$ identifies the radii of curvature and $d_i$ identifies the thicknesses or distances along the optical axis. The index (i) identifies the i-th distance or the i-th face starting at the image plane 12. At this location, it should be noted that the axial distances ($d_3$, $d_5$ and $d_8$) in FIGS. 1b and 1c are shown enlarged for clarity and lie in a region of less than a tenth of a millimeter in correspondence to the optical manufacturing data. In this way, no significant air gaps occur within the endoscope tube.

TABLE I

Beta = −14x

| Radius/m | Distance, Thickness/mm | Glass |
|---|---|---|
| $r_1 = 169.935$ | | |
| | $d_1 = 5.000$ | Air |
| $r_2 = -235.620$ | $d_2 = 2.000$ | SK5 |
| $r_3$ = Planar | $d_3 = 0.010$ | Air |
| $r_4$ = Planar | $d_4 = 286.9$ | Lak10 |
| $r_5 = 43.8165$ | $d_5 = 0.010$ | Air |
| $r_6 = -27.4000$ | $d_6 = 2.000$ | F5 |
| $r_7 = -103.327$ | $d_7 = 1.000$ | SF10 |
| $r_8$ = Planar | $d_8 = 0.010$ | Air |
| $r_9$ = Planar | $d_9 = 177.0$ | SF10 |
| $r_{10} = -15.7244$ | $d_{10} = 1.000$ | Air |
| $r_{11} = 10.4020$ | $d_{11} = 1.000$ | PSK53A |
| $r_{12} = -4.91733$ | $d_{12} = 2.100$ | Air |
| $r_{13} = -20.1614$ | $d_{13} = 1.000$ | SK5 |
| | $d_{14} = 98.24$ | Air |

The embodiment of FIG. 1e is very similar to the embodiment of FIG. 1a. In the embodiment of FIG. 1e, those components which correspond to components in FIG. 1a are each identified by the same reference character.

A significant difference with respect to the embodiment of FIG. 1a is that in FIG. 1e, the field optic 11a is a part of the viewing component 1 and therefore can likewise be used again and again. For this reason, the interface 3a between the viewing component 1 and the endoscope tube 2 extends between the field lens 11a and the glass rod 10. In this way, the field optic 11a can be more complex to provide a better correction of errors. At the same time, the imaging optic in the endoscope tube 2 is simplified. The endoscope tube 2 can, however, only be exchanged with another having an imaging optic exhibiting similar performance data.

The embodiment of FIG. 2a includes an especially simple imaging optic in the endoscope tube 22. This imaging optic comprises only a planar-concave aspherical distal single lens 25, two glass rods (27, 30) and an inner aspherical single lens 28. The two aspherical lenses (25, 28) again conjointly define a telescope system by means of which the object plane 24 is imaged in the intermediate image plane 32. The viewing system includes an ocular 21 having a field lens 31, a direct-vision prism 33 for image reversal, a composite lens 34 and a single lens 35. The chromatic magnification error still present in the intermediate image plane 32 is corrected by the ocular 21. A TV adapter 21a having a further positive composite lens 37 can be mounted selectively proximally of the ocular 21.

Figure 2B:
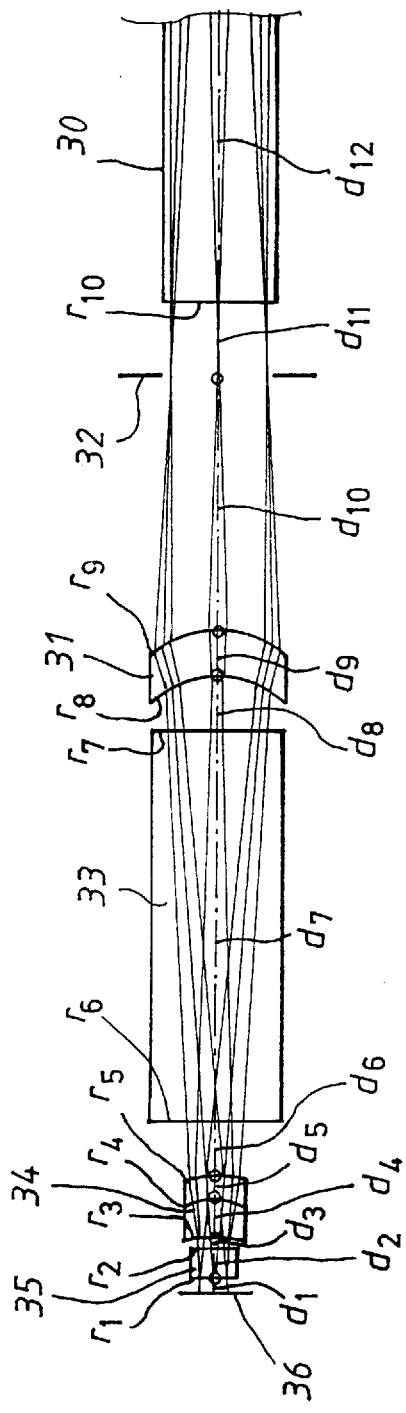
Figure 2C:
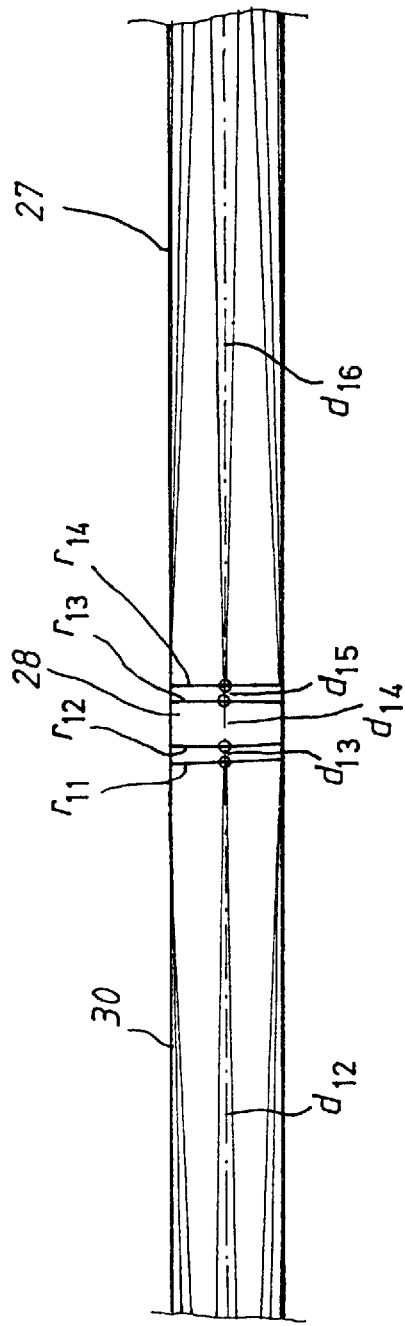

The specific configuration of the embodiment of FIG. 2a is shown in FIGS. 2b to 2d. The optical manufacturing data are given in Table II. Here, the surfaces $r_i$ and the thicknesses or distances $d_1$ starting at the exit pupil 36 of the ocular 21 are identified with increasing numerals. The aspheric constants $C_1$, $C_2$, $C_3$ and $C_4$ of the aspherical surfaces ($r_9$, $r_{13}$ and $r_{16}$) are given with respect to the equation:

$$z = h^2/(2R) + C_1 h^4 + C_2 h^6 + C_3 h^8 + C_4 h^{10}$$

wherein:

R = is the vertex radius of curvature given in Table II;

h = the distance from the optical axis; and, z = arrow elevation (distance from the vertex point in the direction of the optical axis at a spacing h perpendicular to the optical axis).

The distance (h) and the arrow elevation (z) are shown, for example, in FIG. 12 of U.S. patent application Ser. No. 07/833,416, filed February 1992, (PCT patent publication WO 93/15647), incorporated herein by reference.

Reference character $d_{11}$ is the air distance of the intermediate image plane 32 from the end surface $r_{10}$ of the glass rod 30 and $d_{10}$ is the air distance of the intermediate image plane 32 from the next adjacent surface $r_9$ of the field lens 31.

TABLE II

Beta = −11x

| Radius/m | Distance, Thickness/mm | Glass |
|---|---|---|
| $r_1 = -12.9792$ | $d_1 = 1.000$ | Air |
| $r_2 = 1,479.22$ | $d_2 = 2.000$ | SK5 |
| $r_3 = -21.3469$ | $d_3 = 0.500$ | Air |
| $r_4 = -3.25831$ | $d_4 = 2.700$ | PSK53A |
| $r_5 = -6.15685$ | $d_5 = 1.400$ | SFL6 |
| $r_6$ = Planar | $d_6 = 1.000$ | Air |
| $r_7$ = Planar | $d_7 = 42.50$ | BK7 |
| $r_8 = -7.00000$ | $d_8 = 4.000$ | Air |
| $r_9 = -6.49711$ aspheric | $d_9 = 3.000$ | SF10 |
| | $d_{10} = 14.04$ | Air |
| $r_{10}$ = Planar | $d_{11} = 5.000$ | Air |
| $r_{11}$ = Planar | $d_{12} = 179.6$ | LAKN22 |
| $r_{12} = 57.7148$ | $d_{13} = 1.000$ | Air |
| $r_{13} = -77.6781$ aspheric | $d_{14} = 3.000$ | SK2 |
| $r_{14}$ = Planar | $d_{15} = 1.000$ | Air |
| $r_{15}$ = Planar | $d_{16} = 157.1$ | LAKN22 |
| $r_{16} = -3.40247$ aspheric | $d_{17} = 2.000$ | Air |
| $r_{17}$ = Planar | $d_{18} = 1.300$ | SK2 |
| | $d_{19} = 60.00$ | Air | aspheric constants:

| | surface $r_9$ | surface $r_{13}$ | surface $r_{16}$ |
|---|---|---|---|
| $C_1 =$: | $-0.3046321 \times 10^{-3}$ | $0.1540405 \times 10^{-5}$ | $-0.9608183 \times 10^{-3}$ |
| $C_2 =$: | $0.3495135 \times 10^{-5}$ | $0.3849381 \times 10^{-7}$ | $-0.1248615 \times 10^{-4}$ |
| $C_3 =$: | $-0.4623003 \times 10^{-6}$ | $-0.1641962 \times 10^{-8}$ | $-0.2921977 \times 10^{-6}$ |
| $C_4 =$: | $0.9325222 \times 10^{-8}$ | $-0.5966613 \times 10^{-18}$ | $-0.2824844 \times 10^{-7}$ |

The imaging optic has an imaging scale of (−11×). Thus, the plane 24 is reduced by a factor of 11 when imaged in the intermediate image plane 32. The object-end angle (w) of field of view is 60°. Together with the corresponding object distance $d_{19}$ of approximately 60 mm and the object-end numerical aperture of NA=0.0028, a light transmission value of L=0.1 results. This light transmission value is essential for the image brightness of the endoscope image. The transmission of the endoscope computed from the light transmission value corresponds approximately to the transmission of commercially available endoscopes.

Notwithstanding the simple configuration of the imaging optic, this optic is corrected and provides diffraction limited imaging and the distortion amounts to only 6.1% and therefore is comparable to commercially available endoscopes. The chromatic magnification error which is still present in the intermediate image 32 is corrected by the field lens 31. It is advantageous for the transmission in the endoscope that beam guidance in the endoscope tube is free of vignetting. In this way, no disturbing scatter radiation occurs so that no separate measures are required to suppress disturbing stray reflections. The clear diameter of the optic in the endoscope tube amounts to 7.3 mm.

In FIGS. 3a to 3c, the lens section of an embodiment is shown with a viewing ocular and exclusively spherical surfaces. The corresponding optical manufacturing data are listed in Table III.

The radii of curvature $r_i$ of the surfaces and the distances or thicknesses $d_i$ are then again numbered with increasing numerals from the proximal end. Here, $r_1$ is the proximal end surface of the composite lens 43 of the ocular and $d_1$ is the distance of the exit pupil from this surface. The reference character $d_{22}$ is the object distance and $d_{10}$ and $d_{11}$ identify the distances between the intermediate image plane 42 from the field optic 41 and between this plane and the next-adjacent glass rod 40, respectively. The two-lens field optic 41 together with the composite lens 43 and the direct-vision prism 44 conjointly define an ocular for image reversal. Here too, the interface between the endoscope tube and the viewing component (41, 43, 44) is mounted between the field optic 41 and the glass rod 40.

TABLE III

| Beta = −10x | | |
|---|---|---|
| Radius/m | Distance, Thickness/mm | Glass |
| $r_1$ = −16.5542 | $d_1$ = 3.000 | Air |
| $r_2$ = −5.50056 | $d_2$ = 2.700 | BAF4 |
| $r_3$ = −10.3986 | $d_3$ = 1.400 | SFL56 |
| $r_4$ = Planar | $d_4$ = 1.000 | Air |
| $r_5$ = Planar | $d_5$ = 42.50 | BK7 |
| $r_6$ = −25.8047 | $d_6$ = 1.000 | Air |
| $r_7$ = −14.6015 | $d_7$ = 3.000 | SK2 |
| $r_8$ = −203.234 | $d_8$ = 0.500 | Air |
| $r_9$ = −42.1364 | $d_9$ = 3.000 | SK2 |
| $r_{10}$ = Planar | $d_{10}$ = 19.78 | Air |
| | $d_{11}$ = 5.000 | Air |
| $r_{12}$ = Planar | $d_{12}$ = 189.9 | LAKN22 |

TABLE III-continued

| Beta = −10x | | |
|---|---|---|
| Radius/m | Distance, Thickness/mm | Glass |
| $r_{13}$ = 49.1071 | $d_{13}$ = 1.000 | Air |
| | $d_{14}$ = 2.000 | BAF4 |
| $r_{14}$ = −20.6765 | $d_{15}$ = 1.000 | SF10 |
| $r_{15}$ = −59.1285 | $d_{16}$ = 1.000 | Air |
| $r_{16}$ = Planar | $d_{17}$ = 145.0 | LAKN22 |
| $r_{17}$ = Planar | $d_{18}$ = 1.000 | Air |
| $r_{18}$ = −6.08263 | $d_{19}$ = 1.000 | SK2 |
| $r_{19}$ = 85.6204 | $d_{20}$ = 2.100 | Air |
| $r_{20}$ = −5.19296 | $d_{21}$ = 1.000 | SK2 |
| $r_{21}$ = −14.1286 | $d_{22}$ = 60.00 | Air |

In the embodiment of Table II, the distance between the distal front surface $r_{17}$ of the front element and the first intermediate image plane 32 is shortened to a spacing of 350 mm. Likewise, in the embodiment of Table III, the distance between the distal front surface $r_{20}$ of the front element and the first intermediate image plane 42 is reduced to a distance of 350 mm. This distance of 350 mm is often adequate in the area of medicine. These embodiments have a light transmitting value of approximately 0.1. The field optic (31, 41) is mounted behind the intermediate image plane (32 or 42) when viewed from the distal end. The interface between the viewing component and the endoscope tube is arranged between the field optic (31 or 41) and the end face $r_{10}$ of the glass rod (30 or 40) adjacent to the intermediate image plane (32 or 42).

The diameter of the image or intermediate image in all embodiments of Tables I to III is 6.4 mm.

In the endoscope according to the invention, a portion of the lenses and the glass rods (7, 10) can be produced by pressure molding. Insofar as suitable materials are available, the lenses and glass rods can also be made utilizing plastic lenses.

It is understood that the foregoing description is that of the preferred embodiments of the invention and that various changes and modifications may be made thereto without departing from the spirit and scope of the invention as defined in the appended claims.

What is claimed is:

1. An endoscope for viewing an object, the endoscope comprising:

an endoscope tube component;

said endoscope tube component including a tube and an imaging optic arrangement mounted in said tube;

said imaging optic arrangement including a distal front lens group and an inner lens group;

said front lens group and said inner lens group conjointly defining an optical system forming a real image of said object in a plane without intermediate images being formed between said object and said plane;

said plane being located a distance (T) from said front lens group;

said distance (T) being in the range of 200 to 600 mm;

said inner lens group being a single composite lens; and, a field lens mounted in the vicinity of said plane for coacting with said front lens group to compensate for field imaging errors.

2. The endoscope of claim 1, said inner lens group being located at a first distance away from said front lens group; said real image plane being at a second distance from said inner lens group; and, said first distance being equal to or less than said second distance.

3. The endoscope of claim 1, said optical system having a focal length; said front lens group having a negative refractive power and said inner lens group having a positive refractive power; and, said front lens group having a negative diffractive power and said inner lens group having a positive diffractive power so that said front lens group and said inner lens group conjointly define a telesystem having an intercept distance less than said focal length of said optical system.

4. The endoscope of claim 1, said imaging optic arrangement including less than seven lenses.

5. The endoscope of claim 1, said imaging optic arrangement including less than five lenses.

6. The endoscope of claim 1, said endoscope tube component defining an optical axis; said inner lens group having a first surface transverse to said axis and facing said front lens group and a second surface transverse to said axis and facing away from said front lens group; and, said imaging optic arrangement further including: a first glass rod mounted in said tube between said first surface and said front lens group; and, a second glass rod mounted in said tube next to said second surface.

7. The endoscope of claim 6, further comprising a viewing component; and, said viewing component including said field lens adjacent said second glass rod.

8. The endoscope of claim 1, said front lens group being made of a glass resistant to acid.

9. The endoscope of claim 8, said front lens group comprising a single planar-concave lens having a distal end surface; and, said distal end surface being planar.

10. The endoscope of claim 1, said inner lens group having a first surface transverse to said axis and facing said front lens group and a second surface transverse to said axis and facing away from said front lens group; and, said imaging optic arrangement further including: a field lens mounted in said tube adjacent said second surface of said inner lens group; a first glass rod mounted in said tube between said first surface and said front lens group; and, a second glass rod mounted in said tube between said second surface and said field lens.

11. The endoscope of claim 1, additionally comprising a viewing component, said endoscope tube component and said viewing component conjointly defining an optical axis and an interface transverse to said axis whereat said endoscope tube component and said viewing component are mutually connected and disconnected.

12. An endoscope for viewing an object, the endoscope comprising:
    an endoscope tube component;
    said endoscope tube component including a tube and an imaging optic arrangement mounted in said tube;
    said imaging optic arrangement including a distal front lens group and an inner lens group;
    said front lens group and said inner lens group conjointly defining an optical system forming a real image of said object in a plane without intermediate images being formed between said object and said plane;
    said plane being located a distance (T) from said front lens group;
    said distance (T) being in the range of 200 to 600 mm;
    said inner lens group being a single lens; and,
    a field lens mounted in the vicinity of said plane for coacting with said front lens group to compensate for field imaging errors.

13. The endoscope of claim 12, said inner lens group being located at a first distance away from said front lens group; said real image plane being at a second distance from said inner lens group; and, said first distance being equal to or less than said second distance.

14. The endoscope of claim 12, said optical system having a focal length; said front lens group having a negative refractive power and said inner lens group having a positive refractive power; and, front lens group having a negative diffractive power and said inner lens group having a positive diffractive power so that said front lens group and said inner lens group conjointly define a telesystem having an intercept distance less than said focal length of said optical system.

15. The endoscope of claim 12, said imaging optic arrangement including less than seven lenses.

16. The endoscope of claim 12, said imaging optic arrangement including less than five lenses.

17. The endoscope of claim 12, said endoscope tube component defining an optical axis; said inner lens group having a first surface transverse to said axis and facing said front lens group and a second surface transverse to said axis and facing away from said front lens group; and, said imaging optic arrangement further including: a first glass rod mounted in said tube between said first surface and said front lens group; and, a second glass rod mounted in said tube next to said second surface.

18. The endoscope of claim 17, further comprising a viewing component; and, said viewing component including said field lens adjacent said second glass rod.

19. The endoscope of claim 12, said front lens group being made of a glass resistant to acid.

20. The endoscope of claim 19, said front lens group comprising a single planar-concave lens having a distal end surface; and, said distal end surface being planar.

21. The endoscope of claim 12, additionally comprising a viewing component, said endoscope tube component and said viewing component conjointly defining an optical axis and an interface transverse to said axis whereat said endoscope tube component and said viewing component are mutually connected and disconnected.

22. An endoscope for viewing an object, the endoscope comprising:
    an endoscope tube component;
    said endoscope tube component including a tube and an imaging optic arrangement mounted in said tube;
    said imaging optic arrangement including a distal front lens group and an inner lens group;
    said front lens group and said inner lens group conjointly defining an optical system forming a real image of said object in a plane without intermediate images being formed between said object and said plane;
    said plane being located a distance (T) from said front lens group;
    said distance (T) being in the range of 200 to 600 mm; and,
    said inner lens group being a single composite lens.

23. An endoscope for viewing an object, the endoscope comprising:
    an endoscope tube component;
    said endoscope tube component including a tube and an imaging optic arrangement mounted in said tube;

said imaging optic arrangement including a distal front lens group and an inner lens group;

said front lens group and said inner lens group conjointly defining an optical system forming a real image of said object in a plane without intermediate images being formed between said object and said plane;

said plane being located a distance (T) from said front lens group;

said distance (T) being in the range of 200 to 600 mm; and, said inner lens group being a single lens.

* * * * *